United States Patent [19]

Tamburrino

[11] Patent Number: 5,202,758
[45] Date of Patent: Apr. 13, 1993

[54] FLUORESCENT PENETRANT MEASUREMENT BORESCOPE

[75] Inventor: Richard A. Tamburrino, Auburn, N.Y.

[73] Assignee: Welch Allyn, Inc., Skaneateles Falls, N.Y.

[21] Appl. No.: 760,495

[22] Filed: Sep. 16, 1991

[51] Int. Cl.⁵ .............................................. H04N 7/18
[52] U.S. Cl. ...................................... 358/98; 128/6; 250/461.1
[58] Field of Search ................. 358/98, 107, 117, 110; 128/6, 4; 250/461.1; 324/219

[56] References Cited

U.S. PATENT DOCUMENTS

| | | | |
|---|---|---|---|
| 4,302,678 | 11/1981 | Schiffert | 250/461.1 |
| 4,538,182 | 8/1985 | Saito et al. | 358/280 |
| 4,707,713 | 11/1987 | Ayata et al. | 346/140 |
| 4,853,774 | 8/1989 | Danna et al. | 358/98 |
| 4,855,765 | 8/1989 | Suzuki et al. | 346/156 |
| 4,873,570 | 10/1989 | Suzuki et al. | 358/80 |
| 4,980,763 | 12/1990 | Lia | 358/98 |
| 4,998,166 | 3/1991 | Salvati | 358/98 |
| 5,061,995 | 10/1991 | Lia et al. | 358/98 |

Primary Examiner—James J. Groody
Assistant Examiner—Glenton B. Burgess
Attorney, Agent, or Firm—Wall and Roehrig

[57] ABSTRACT

A fluorescent borescope is provided that provides target measuring capabilities. The device includes a primary ultraviolet light source and a secondary visible light source that has a light path spaced apart from the primary light source. The secondary light source is associated with a shadow bar that projects a shadow onto a target to be measured in a way that its video image changes position or size in proportion to the distance of the image sensing head of the borescope from the target. Calibration and measurement circuitry are provided to determine the size of the target in relation to the magnification of the projected shadow.

9 Claims, 2 Drawing Sheets

FLUORESCENT PENETRANT MEASUREMENT BORESCOPE

BACKGROUND OF THE INVENTION

This invention relates to a fluorescent borescope for providing a full color video image of a generally inaccessible target that fluoresces when illuminated with ultraviolet light, and more particularly to an apparatus for measuring the size of fluorescent targets viewed on the image display of the borescope.

Borescopes have been provided in the prior art for realizing a black-and-white or full color video picture of a generally inaccessible target that is situated within a cavity and therefore cannot be viewed using direct vision. They are commonly used to identify cracks or defects in the structure of remote, inaccessible surfaces of industrial machinery such as pipes within steam generating equipment, aircraft, and other equipment where structural integrity is important to safe operation.

Fluorescence penetrant borescopy is a well known technique for finding cracks or defects. To perform this technique, a chemical compound that acts as a penetrant is applied to the surface to be viewed and time allowed for penetration into surface discontinuities. After removal of excess penetrant the surface is treated with a developer that has a blotting action, so that the compound will be drawn out from the discontinuities onto the surface where it fluoresces when exposed to ultraviolet light. The fluorescence can then be visualized as an indication through a rigid or a flexible borescope.

Heretofore when using fluorescence penetrant borescopy, all attempts to measure the image on the video display to determine the size of the target being viewed have utilized mechanical accessories. One approach requires the placing of a known scale adjacent to the image to be measured for a comparison measurement. Alternatively a physical standoff can be provided over the lens on the end of the borescope insertion tube at which point the magnification is known. By adjusting the end of the borescope until it just touches the target to be viewed at the standoff, the image will appear on the screen at a known magnification, whereupon it can be measured and its precise size determined. While these methods of measurement are effective, they remain somewhat awkward and painstaking, and improvements have been desired.

It is taught in U.S. Pat. No. 4,980,763 to Lia of common assignee herewith, that targets illuminated through a borescope by a general illumination source can be measured by creating an auxiliary image having a known characteristic, such as a shadow, and projecting it on the target in such a way that its position or size changes in proportion to the distance of the image sensing head from the target. An auxiliary illumination source means is commonly used to generate the auxiliary image. A precalibrated target magnification and distance overlay for the geometry of the borescope is placed on the video display to indicate the magnification factor for the physical measurement of the target on the display screen. Alternatively electronic calibration and measurement circuitry can be provided. This is known as the shadow measurement technique. The art of shadow measurement has been more recently advanced by modifications of the illumination system in borescopes. A typical improved device is found in a co-pending application, Ser. No. 573,870, entitled "Apparatus and Method for Selecting Fiber Optic Bundles in a Borescope", and assigned to the Assignee of the present Application.

In the prior art devices the target to be viewed is illuminated by light transmitted through at least two separate fiber optic illumination bundles, and means are provided for selectively illuminating one or the other, or both of the bundles, depending on the illumination desired on the target to be viewed. A general light source operates through a first fiber optic bundle and illuminates the target. An auxiliary fiber optic bundle is typically configured as a thin strip extending across the first fiber optic bundle, and an opaque index element or bar is positioned a preassigned spaced distance in front of the termination of the auxiliary fiber optic bundle. When the auxiliary fiber optic bundle is actively carrying light, a shadow is cast by the opaque index element onto the target being viewed.

Shadow measurement has not been practicable with fluorescent borescopes because of insufficient illumination. To achieve acceptable accuracy, relatively small optical fiber bundles that emit correspondingly small amounts of light have been used in the prior art to generate the shadow image. Furthermore, light losses occur in the filters required for certain fluorescent optical instruments. These factors and small target indication sizes combine to limit the visibility of the shadow that is projected.

SUMMARY OF THE INVENTION

It is therefore a primary object of the present invention to apply the shadow measurement technique to fluorescence penetrant measurement borescopy.

It is a further object of the invention to provide a target measuring system in a fluorescence measurement borescope that is self-contained and integral with the illumination and sensor systems of the borescope.

It is another object of the invention to provide a target measuring system for a fluorescent borescope that can be operated entirely external to the cavity into which the borescope insertion tube is placed.

It is yet another object of the invention to provide an illumination system for a full color video image device that additionally provides a measuring indicator for determining object distance from the lens assembly of the video imaging device in a fluorescent borescope.

It is still another object of the present invention to provide a target measuring system in a fluorescent borescope for electronically measuring the size of a target being viewed.

These and other objects of the present invention are attained by a target illumination system which provides for illumination of the target to be viewed by light transmitted from two sources, one of which transmits blue or ultraviolet light and does not include project shadows. Another source transmits visible light and is associated with a structure adapted to shadow projection. Either or both of the light sources may be selectively enabled, in accordance with the illumination desired on the target to be viewed.

BRIEF DESCRIPTION OF THE DRAWINGS

For a better understanding of these and other objects of the present invention, reference is made to the detailed description of the invention which is to be read in conjunction with the following drawings, wherein.

DETAILED DESCRIPTION OF THE INVENTION

Figure 1:
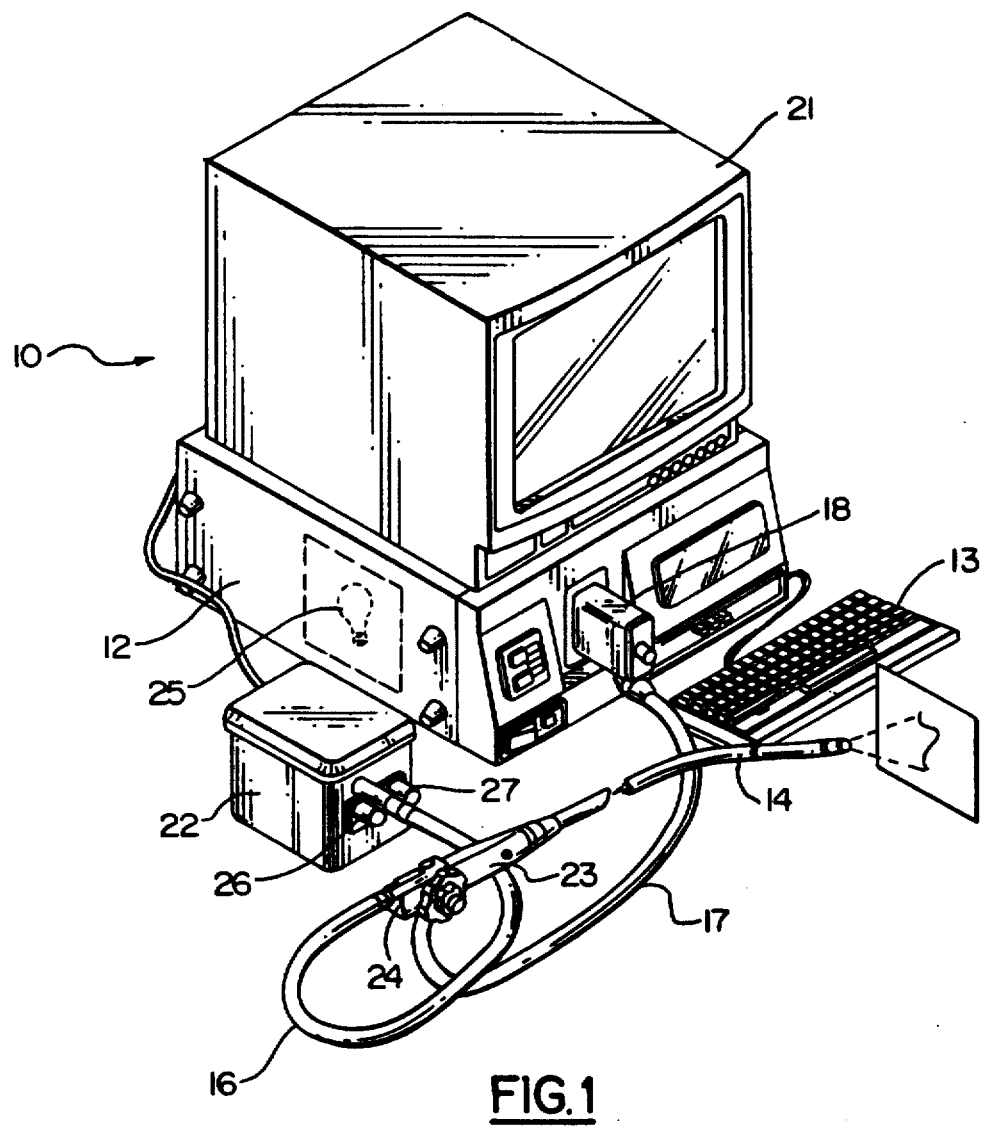
FIG. 1 is a perspective view of a system embodying the teachings of the present invention.
Figure 3:
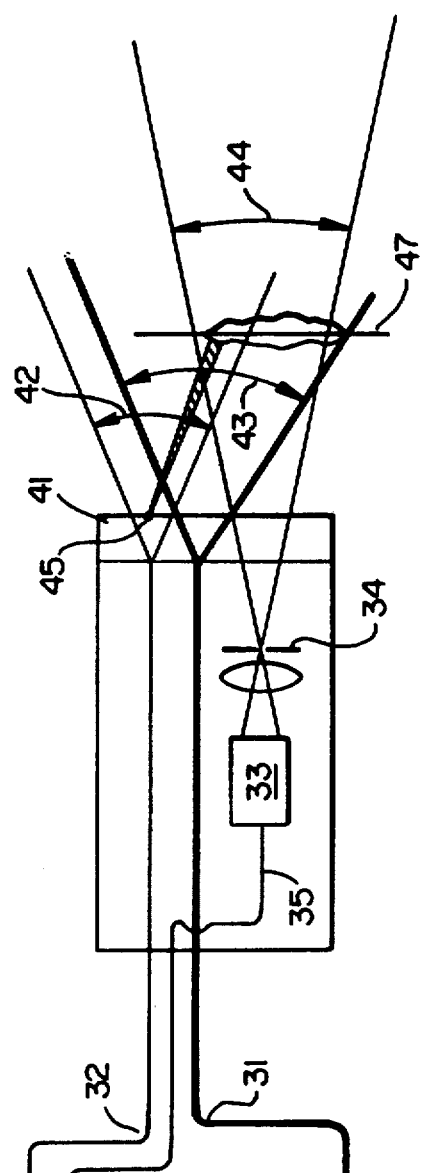
FIG. 3 is a schematic representation of the system of FIG. 1.

Turning now to the drawings, and in particular FIGS. 1 and 3, there is shown generally at 10 a borescope system in accordance with the present invention. Housing 12 contains conventional electronics for video processing and for interaction with the operator via keyboard 13. An insertion tube 14 is inserted into the cavity which is to be inspected and includes fiber optic bundle 31 for transmission of ultra-violet or blue light, and fiber optic bundle 32 for transmission of visible light. Both bundles generally terminate at the distal end of insertion tube 14. When ultraviolet light is employed bundle 31 is constructed of a material that will readily transmit ultraviolet light, such as quartz. It is possible to transmit blue light through bundle 31, in which case it can be constructed of a material such as glass. But if the latter construction is elected, a 460 nm bandpass filter (not shown) or similar filter must be incorporated into the optical path for removing wave components that may interfere with visualization of fluorescence, between the optics 34 and the object 47. Light passing through bundle 31 causes a suitably treated illuminated surface to fluoresce when discontinuities are present in the surface. Knob 27 permits the operator to swing in 460 nm bandpass filter to generate blue light.

In the particular embodiment of the invention shown in FIG. 1, the fiber optic bundles 31, 32 are carried in umbilicals 16 and 17 respectively, connecting with videoprocessor 35 via electronics adaptor 18, and with ultra-violet light source 22. However the invention is broad enough to include alternative embodiments, wherein the light sources could be provided in the distal end of the insertion tube.

The insertion tube or probe 14 incorporates an optical pickup or video retrieval device 33 with suitable optics 34. The video retrieval device can be a camera, a coherent optical fiber bundle, or a relay lens system. As an optical fiber bundle is commonly employed, the invention will be discussed in conjunction therewith; however the invention can be used with any conventional video retrieval device.

Information detected by video retrieval device 33 is relayed via channel 35 to videoprocessor 36 that includes electronics, a display unit 21, and a computer for image processing and interaction with the operator.

An ultraviolet or blue light source 22 is fed through fiber optic bundle 31. A source of visible light, such as xenon discharge lamp 25, transmits light through fiber optic bundle 32. In the embodiment represented by FIG. 1, the xenon lamp 25 is integral with videoprocessor 12, and the ultraviolet light source 22 may also be constructed integral with the videoprocessor. Lines 39, carry control and synchronization signals to the light sources from the videoprocessor. A control knob 26 is provided to allow variation in the intensity of light source 22. Keyboard 13 allows operator interaction with the videoprocessor, and in particular allows the operator to invoke image enhancement algorithms that are implemented in the videoprocessor.

Borescope imager head 41 contains the terminations of fiber optic bundles 31 and 32. Overlapping arcs 42 and 43 are respectively illuminated by visible light source 25 and ultraviolet light source 22. The field of view is determined by the optics 34 that may include a lens system, and is represented by arc 44 in FIG. 3. The fiber optic bundle 32 is disposed in close proximity to bundle 31, and provides enough general illumination to effectively visualize a structure that may contain an indication. Because bundles 31 and 32 are not superimposed as in the prior art, it is feasible to use relatively large fibers that deliver abundant light to the illuminated field. Positioned a spaced distance in front of the termination of fiber optic bundle 32 is an opaque index element or shadow bar 45 that extends the full width of bundle 32 and casts a shadow from the illumination emanating from fiber optic bundle 32 onto the target and indications being viewed. The shadow and an indication located at line 27 will appear on the display 21, and can be viewed in conjunction with one another. The indication can then be measured, using the shadow as a reference. The above noted U.S. Pat. No. 4,980,763 to Lia teaches the measurement of a target through a borescope by evaluation of a changing parameter of a contrasting shadow and is hereby incorporated by reference.

Figure 2:
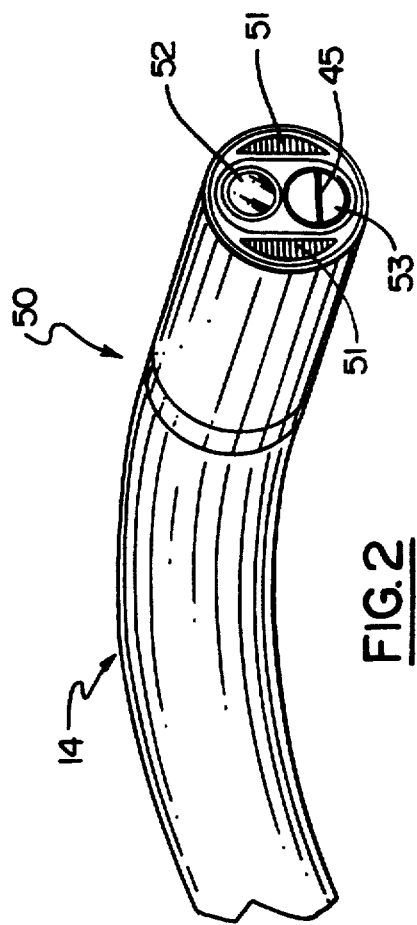
FIG. 2 is an enlarged fragmentary view of the distal end of an insertion tube of the system of FIG. 1.

In the particular embodiment of the invention represented in FIG. 2, there is shown generally at 50 the distal end of insertion tube 14, wherein the fiber optic bundle 31 carrying ultra-violet or blue light terminates in two diametrically opposed arcs 51, 51 on the plane of the distal end of the insertion tube. The termination 53 of visible light carrying fiber optic bundle 32 and window 52 are disposed intermediate arcs 51,51. Window 52 allows light reflected from illuminated targets to reach video retrieval device 33. Opaque shadow bar 45 is positioned closely adjacent the termination of fiber optic bundle 32, in the path of emitted visible light, and spanning the area comprising termination 53. The bar is offset from the optical axis of fiber optic bundle 32, so that a contrasting shadow is cast on the field of illumination.

The illumination sources are selectable by the operator. An indication is normally identified in the fluorescent penetration method by viewing under black (ultraviolet or filtered blue) light. For taking quantitative measurements the visible light source is enabled, and its intensity adjusted until the shadow becomes visible in conjunction with the indication or target being viewed. Once the shadow and the target have been acquired on the video display unit, measurement proceeds in accordance with the procedures explained in the Lia patent.

With the embodiment of FIGS. 1-3 it is possible to perform fluorescent penetrant borescopy, or simply view the surface under general visible light as in the case of a non-fluorescent borescope. This dual function is possible without significant increase in the diameter of the borescope insertion tube. Non-fluorescent features may be measured by bringing into play the shadow processing features of the video display and videoprocessor, and the operator may selectively enable and independently adjust the intensity of the light sources by interaction with the system through keyboard 13 or controls 24 (shown in FIG. 1), located at the proximal end of the insertion tube.

While this invention has been explained with reference to the structure disclosed herein, it is not confined to the details set forth and this application is intended to cover any modifications and changes as may come within the scope of the following claims:

What is claimed is:

1. A fluorescent type borescope having an elongated insertion tube that has a proximal end, a distal end, a distally disposed optical pickup for viewing remotely located targets, and target measuring means including:
   a first light source that emits light causing an illuminated indication to fluoresce;
   a second light source that emits visible light;
   auxiliary image creating means operatively associated with said second light source, and being disposed to cause an image created to change at least one characteristic in proportion to the distance between an indication to be measured and the distal end of said insertion tube;
   measuring means for determining the change in characteristic of said created image, so that the true physical size of the indication to be measured can be determined;
   a first fiber optic bundle extending from said proximal end to said distal end of said insertion tube and being connected to said first light source; and
   a second fiber optic bundle extending from the proximal end to the distal end of said insertion tube, having an optical axis, and being connected to said second light source, said first and second fiber optic bundles terminating in spaced apart relationship at the distal end of the insertion tube, whereby a target that may include an indication can be viewed.

2. The borescope of claim 1, wherein said first light source emits ultraviolet light.

3. The borescope of claim 1, wherein said image creating means comprises a shadow bar that is disposed in a path of light being emitted by said second light source, whereby a shadow line is created on the indication being viewed and on the image thereof.

4. The borescope of claim 1, further including bandpass filter means for removing wave components that may interfere with visualization of fluorescence.

5. The borescope of claim 1, wherein said image creating means comprises a shadow bar positioned closely adjacent the termination of said second fiber optic bundle and offset from the optical axis of said second fiber optic bundle so that a shadow line is created on the indication being viewed and on the image thereof.

6. The borescope of claim 1, wherein said measurement means comprises a video display, circuit means for counting pixels in said video display from one edge thereof to an image displayed thereon, and means for determining said parameter of said contrasting shadow.

7. The borescope of claim 6, further including cursors for locating a starting pixel and an ending pixel so that pixels are counted therebetween.

8. A method of quantitative fluorescence penetrant borescopy, comprising the steps of:
   illuminating a surface with a first light source that is projected through a borescope through a first fiber optic bundle, said first light source being capable of exciting fluorescence on indications that may be on said surface;
   illuminating the surface with a second light source that is projected through the borescope through a second fiber optic bundle that terminates within said borescope in spaced apart relationship to said first fiber optic bundle, said second light source being operatively associated with an auxiliary image creating means, whereby said second light source and said auxiliary image creating means cast a contrasting shadow on the surface that can be viewed in conjunction with said fluorescing indications;
   viewing an image of the surface through said borescope; and
   measuring a fluorescent indication in accordance with a parameter of the contrasting shadow, wherein said parameter varies with the distance between said auxiliary image creating means and the surface.

9. A method of quantitative fluorescence penetrant borescopy, comprising the steps of:
   applying a penetrant to a surface to be examined;
   removing excess penetrant;
   treating said target with a developer that has a blotting action, whereby penetrant that is retained within discontinuities in the surface are drawn onto the surface;
   illuminating the surface with a first light source that is projected through a borescope through a first fiber optic bundle, whereby the penetrant fluoresces;
   viewing an image of the surface through said borescope;
   identifying fluorescing indications on the surface;
   illuminating the surface with a second light source that is projected through the borescope through a second fiber optic bundle that terminates within said borescope in spaced apart relationship to said first fiber optic bundle, said second light source being operatively associated with an auxiliary image creating means, whereby said second light source and said auxiliary image creating means cast a contrasting shadow on the surface that can be viewed in conjunction with said fluorescing indications;
   measuring an indication in accordance with a parameter of the contrasting shadow, wherein said parameter varies with the distance between said auxiliary image creating means and the surface.

* * * * *